United States Patent
Ascione et al.

(10) Patent No.: US 12,213,878 B2
(45) Date of Patent: Feb. 4, 2025

(54) HEART VALVE

(71) Applicants: THE UNIVERSITY OF BRISTOL, Bristol (GB); CAMBRIDGE ENTERPRISE LIMITED, Cambridge (GB)

(72) Inventors: Raimondo Ascione, Bristol (GB); Geoffrey Moggridge, Cambridge (GB); Joanna Stasiak, Cambridge (GB); Marta Serrani, Cambridge (GB); Eugenia Biral, Cambridge (GB)

(73) Assignees: THE UNIVERSITY OF BRISTOL, Bristol (GB); CAMBRIDGE ENTERPRISE LIMITED, Cambridge (GB)

( * ) Notice: Subject to any disclaimer, the term of this patent is extended or adjusted under 35 U.S.C. 154(b) by 692 days.

(21) Appl. No.: 17/434,724

(22) PCT Filed: Feb. 28, 2020

(86) PCT No.: PCT/GB2020/050491
§ 371 (c)(1),
(2) Date: Aug. 27, 2021

(87) PCT Pub. No.: WO2020/174253
PCT Pub. Date: Sep. 3, 2020

(65) Prior Publication Data
US 2022/0125580 A1    Apr. 28, 2022

(30) Foreign Application Priority Data
Feb. 28, 2019 (GB) .................... 1902717

(51) Int. Cl.
*A61F 2/24* (2006.01)
*B29C 45/00* (2006.01)
(Continued)

(52) U.S. Cl.
CPC .......... *A61F 2/2415* (2013.01); *A61F 2/2418* (2013.01); *B29C 45/0001* (2013.01);
(Continued)

(58) Field of Classification Search
CPC ........ A61F 2/24; A61F 2/2412; A61F 2/2415; A61F 2/2418; B29C 45/0001;
(Continued)

(56) References Cited

U.S. PATENT DOCUMENTS

2008/0249614 A1    10/2008    Wang et al.
2014/0005772 A1    1/2014    Edelman et al.
(Continued)

FOREIGN PATENT DOCUMENTS

EP    2208518 A2    7/2010
WO    2013-055977 A1    4/2013
(Continued)

OTHER PUBLICATIONS

Seung Bum Chun et al., Macromolecules, 1999, vol. 32, No. 12, pp. 4030-4042.
(Continued)

*Primary Examiner* — Dinah Baria
(74) *Attorney, Agent, or Firm* — Harness, Dickey & Pierce, P.L.C.

(57) ABSTRACT

A method of manufacturing a heart valve comprises: a step of injection moulding a first part of the heart valve from a first block-copolymer, wherein the injection moulding is performed at a temperature below an order-disorder transition temperature of the block copolymer, such that a phase structure is present in the molten block-copolymer; a step of injection moulding a second part of the heart valve from a second block-copolymer that is different to the first block-copolymer, by over-moulding over the first part to form an over-moulded structure, wherein the injection moulding is
(Continued)

performed at a temperature below order-disorder transition temperatures for the first and second block copolymers, such that a phase structure is present in the molten second block-copolymer and remains present in the first block-copolymer; and a step of cooling the over-moulded structure, without heating it above the order-disorder transition temperatures between the step of injection moulding the second part and the step of cooling, so as to preserve an arrangement of the phase structures created during the steps of injection moulding and produce anisotropic physical properties in the second part.

24 Claims, 7 Drawing Sheets

(51) Int. Cl.
    *B29C 45/16*     (2006.01)
    *B29C 45/72*     (2006.01)
    *B29K 25/00*     (2006.01)
    *B29K 105/00*     (2006.01)
    *B29L 31/00*     (2006.01)

(52) U.S. Cl.
    CPC ...... *B29C 45/1679* (2013.01); *B29C 45/7207* (2013.01); *B29K 2025/08* (2013.01); *B29K 2105/0085* (2013.01); *B29K 2995/0044* (2013.01); *B29K 2995/0082* (2013.01); *B29L 2031/7534* (2013.01)

(58) Field of Classification Search
    CPC ............ B29C 45/1679; B29C 45/7207; B29K 2025/08; B29K 2105/0085; B29K 2995/0044; B29K 2995/0082
    See application file for complete search history.

(56) References Cited

U.S. PATENT DOCUMENTS

2015/0073537 A1*   3/2015   Jimenez ................ A61F 2/2409
                                                                                                                                      623/2.11
2016/0296323 A1   10/2016   Wulfman et al.
2017/0014546 A1*   1/2017   Moggridge ........... A61F 2/2415

FOREIGN PATENT DOCUMENTS

WO     2014-170870 A2   10/2014
WO     2015-128605 A1   9/2015

OTHER PUBLICATIONS

Francesco De Gaetano et al., Fluid Dynamic Characterization of a Polymeric Heart Valve Prototype (Poli-Valve) Tested Under Continuous and Pulsatile Flow Conditions, Int J Artif Organs, Dec. 17, 2015, 38(11), pp. 600-606.

* cited by examiner

HEART VALVE

CROSS-REFERENCE TO RELATED APPLICATIONS

This application is a U.S. National Phase Application under 35 U.S.C. 371 of International Application No. PCT/GB2020/050491, filed on Feb. 28, 2020, which claims priority to Great Britain Patent Application No. 1902717.6, filed on Feb. 28, 2019. The entire disclosures of the above applications are expressly incorporated by reference herein.

FIELD

This invention relates to the provision of a prosthetic heart valve made from block copolymers. Such prosthetic heart valves offers an outstanding balance of durability and biocompatibility.

Prosthetic heart valves are commercially available, and broadly fall into two categories: (i) rigid inorganic/metal valves (for example, made from pyrolytic carbon) and (ii) organic/biological valves formed from animal tissue. Both types of valve have different advantages and disadvantages. The inorganic valves, whilst being very durable, are less biocompatible requiring anticoagulation, and hence have increasing risks of either blood clotting/embolization or bleeding. In contrast, the organic/biological valves do not require anticoagulation, hence have less risk of clotting or bleeding but have a more limited lifespan, since they are constructed from non-inert biological tissue, and are hence prone to degeneration/calcification. Other disadvantages of these prosthetic valves are that they result from the assembling of different parts, made from different materials including fabric, either manually or mechanically Both inorganic and organic valves have rigid sewing rings (covered with fabric), hence once sutured in place they transform the dynamic aortic annulus into a fixed structure. In the case of inorganic/metal valves not only does the aortic annulus become fixed after valve implant, but it is also deformed as these valves impose their 2D geometry to the 3D shape of the aortic valve annulus. In addition, the fabric of the sewing ring with its porosity can easily be colonised by bacteria following sepsis, hence triggering endocarditis.

One area of research has considered the use of organic polymers as an alternative material for creating the artificial valves. However, there are no commercially available polymeric heart valves. Polymeric valves have the potential to combine advantages of mechanical and bioprosthetic valves, with a prospect of long-term durability and no necessity for permanent anticoagulation. Proposed polymeric heart valves are predominantly constructed of polymer-based materials and have good biocompatibility and biostability. As opposed to laborious hand sewing of tissue to frames in existing bioprostheses or of mechanical assembling of inorganic prostheses, polymeric heart valves can be developed by a simple means of fabrication and can be therefore significantly cheaper with no human error. For example, WO 2013/055977 considers the use of a poly(styrene-isobutylene-styrene) (or SIBS) block copolymer, which was selected for its desirable bulk physical properties.

However, valves made of such materials have been unacceptably susceptible to damage and material fatigue due to the repeated stresses of operation. In particular, the valve leaflets, which operate to open and close the valve, undergo particularly high stresses (i.e. large stress concentration) where they are attached to the supporting structure (which is more rigid), and are prone to failure when made of polymer.

Native heart valves exhibit anisotropic material behaviour which is directly related to their microstructure. The valve leaflet tissue consists of layers exhibiting highly anisotropic arrangements of collagen fibres. The fibrosa and ventricularis layers contain circumferentially oriented fibres, with the function of bearing stress during loading. There is also a layer of elastin present, oriented mainly radially in the ventricularis, and its function is to maintain a specific collagen fibre configuration and to return the fibres to their unloaded state intact when the load has been released.

The mechanical anisotropy of human aortic heart valve leaflets is evident in measured values of the elastic modulus, which is much higher in the circumferential direction (measuring 14.5 MPa) than in the radial direction (1.5 MPa).

EP 2,208,518 discusses injection moulding of block-copolymers in the presence of lubricants and other components.

WO 2015/128605 discloses producing heart valves from a single block copolymer.

The present invention aims to provide improved heart valve prostheses by meeting and maintain the demanding functional mechanical requirements, by more closely mimicking the structure and function of native valves.

SUMMARY

According to a first aspect of the present invention there is provided a method of manufacturing a heart valve, the method comprising: a step of injection moulding a first part of the heart valve from a material comprising a first block-copolymer, wherein the injection moulding is performed at a temperature below an order-disorder transition temperature of the first block copolymer, such that a phase structure is present in the molten block-copolymer; a step of injection moulding a second part of the heart valve from a material comprising a second block-copolymer that is different to the first block-copolymer, by over-moulding over the first part to form an over-moulded structure, wherein the injection moulding is performed at a temperature below order-disorder transition temperatures for the first and second block copolymers, such that a phase structure is present in the molten second block-copolymer and remains present in the first block-copolymer; and a step of cooling the over-moulded structure, without heating it above the order-disorder transition temperatures between the step of injection moulding the second part and the step of cooling, so as to preserve an arrangement of the phase structures created during the steps of injection moulding and produce anisotropic physical properties in the second part. This method produces a heart valve with a material phase structure that mimics the structure of a native valve, with varying physical properties in the first and second parts to enable the different parts to perform their different tasks, without introducing particular points of weakness between the different parts. In some cases, the method can also include moulding further (i.e. third etc) parts.

Optionally, the first block copolymer has a higher order-disorder temperature than the second block-copolymer.

Optionally, the first and second block-copolymers are composed of the same constituent monomers.

Optionally, the first and second block-copolymers are both sytrenic block-copolymers, optionally both styrenic triblock-copolymers.

Optionally, the method further comprises a step of annealing the over-moulded structure after the step of injection moulding the second part.

Optionally, the step of annealing comprises maintaining the over-moulded structure at a temperature below the order-disorder temperatures of the first and second copolymers and above the glass transition melting temperatures of the first and second copolymers.

Optionally, the step of annealing lasts for 1 minute or more, optionally 2 minutes or more, further optionally 4 minutes or more.

Optionally, the step of annealing lasts for 10 minutes or less, optionally 8 minutes or less, further optionally 6 minutes or less.

Optionally, the step of cooling comprises lowering the temperature of the over-moulded structure below the glass transition melting temperatures of the first and second block-copolymers.

Optionally, the step of cooling comprises lowering the temperature of the over-moulded structure by 20° C. or more at a rate of 10° C./min or more.

Optionally, the step of cooling occurs before the over-moulded structure is removed from the mould.

Optionally, the first and/or second step of injection moulding occurs at a volumetric flow rate of from 0.1 to 10 cm3/s, optionally from 0.5 to 5 cm3/s, further optionally from 1 to 3 cm3/s.

Optionally, the second part comprises a heart valve leaflet.

Optionally, an injection point for the step of injection moulding the second part is at a centre point of the leaflet.

Optionally, the leaflet is a cylindrical section.

Optionally, the leaflet has a mean thickness in the range of 0.20 mm to 0.70 mm, optionally 0.3 mm to 0.50 mm, further optionally 0.37 mm to 0.42 mm.

Optionally, the second block-copolymer has a lower Young's modulus than the first block-copolymer, optionally wherein the second block-copolymer has an isotropic Young's modulus that is at least 20 MPa less than that of the first block-copolymer, further optionally at least 40 MPa less, still further optionally at least 50 MPa less.

Optionally, the first part comprises a stent.

According to a second aspect of the invention, there is provided a heart valve manufactured according to the method of any preceding claim.

According to a third aspect of the invention, there is provided a heart valve comprising: a first part formed from a material comprising a first block-copolymer exhibiting a phase structure formed by its constituent blocks; and a second part formed from a material comprising a second block-copolymer that is different to the first block-copolymer, the second block copolymer exhibiting a phase structure formed by its constituent blocks, wherein the phase structure of the second block-copolymer is arranged so as to produce anisotropic physical properties in the second part.

Optionally, the second part comprises a heart valve leaflet.

Optionally, the valve leaflet has a variable thickness across its surface.

Optionally, the first part comprises a stent.

Optionally, the stent comprises a sewing ring.

Optionally, the sewing ring comprises holes for passing a sewing needle through.

DRAWINGS

The invention will now be described, by way of example only, with reference to the exemplary Figures, in which.

DETAILED DESCRIPTION

Figure 1:
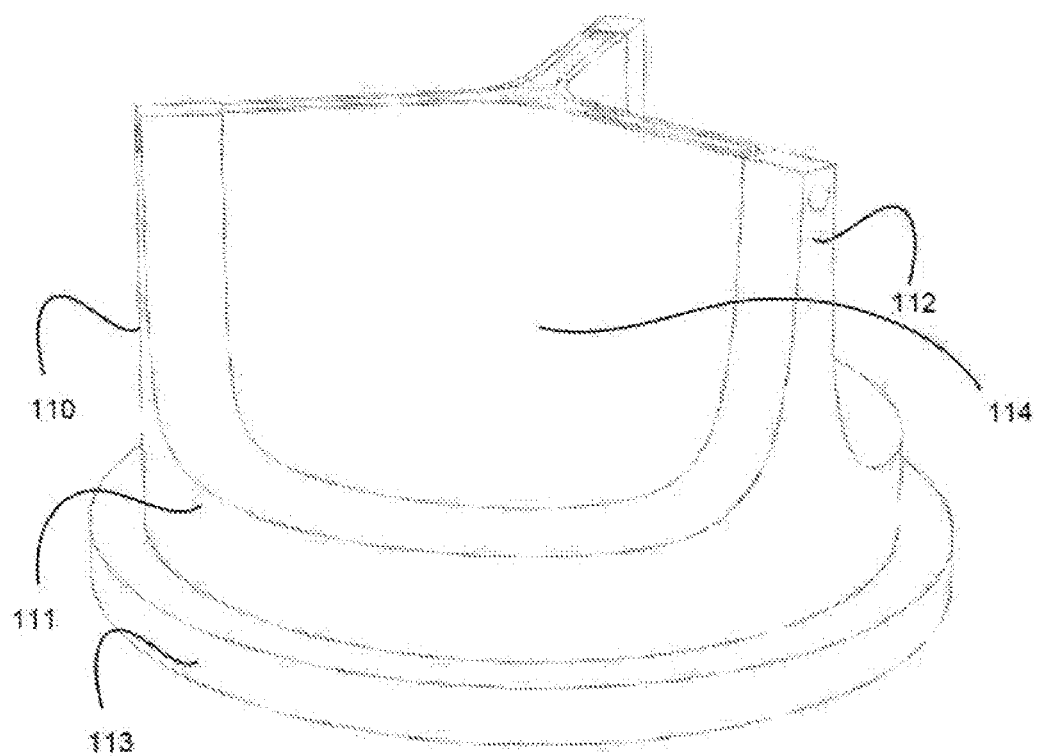
FIG. 1 is a schematic representation of an injection moulded heart valve.

An improved heart valve can be made by producing a valve which more closely mimics the structure of a native valve both at leaflet and at annular levels. This can be achieved by making use of the property of block copolymers (BCPs) to self-assemble into different phase structures. This is discussed in WO 2015/128605, which is hereby incorporated herein in its entirety.

BCPs are a class of polymers that form nano-scale morphologies, due to the presence of 'blocks' of different repeated monomers within the same polymer chain. Below the order-disorder transition (ODT) temperature, the different blocks separate into different phases, but are constrained by bonds within the polymer chains. As a result, different phase structures are produced, depending upon the number of phases present and the relevant volume fractions. Above the ODT temperature, the different phases mix, and no phase structures are seen.

For a two-phase system, approximately equal volume fractions for the two phases will result in a lamellar morphology (i.e. sheets of one phase separated by sheets of the other), whilst reducing the volume fraction of one phase will result (in order of decreasing volume fraction) in the so-called 'gyroid' structure, then cylinders and then spheres of the minor phase in a matrix of the other. As such, it is conventional to specify BCP composition in terms of volume fractions or percentages, and all BCP compositions below are provided as volume fractions or percentages, unless specified otherwise.

The bulk physical properties of BCPs often depend critically on the phase orientation induced during processing, although this orientation requires the processing of the BCP below the ODT temperature.

A BCP processed above the ODT temperature will not develop any phase structure, and if cooled in a quiescent state will develop randomly oriented micro-domains of phase structures equivalent to a polycrystalline structure. In contrast, for example, in thermoplastic elastomers with a cylindrical morphology processed below the ODT, the alignment of the cylindrical phase structures results in orthotropic mechanical properties.

As such, where BCPs are selected for use due to their generic bulk properties (e.g. in WO 2013/055977) and isotropic properties are desired, no effort is made to orient or align the nanophases, resulting in the aforesaid polycrystalline structure with micro-regions of alignment in different directions (or, as in WO 2013/055977, in which the polymer is heated and then cross-linked, the nanophases can be destroyed and prevented from re-forming at all).

Cylinder-forming block copolymers have been known to orient strongly in the direction of flow when confined to a channel e.g. in a channel die or during extrusion. This results in strongly anisotropic mechanical properties, with (for the case of styrenic cylinders in a rubbery matrix) a higher Young's modulus in the direction of orientation of the cylinders.

As discussed in WO 2015/128605, a different type of orientation can be seen in injection moulded films. Anisotropic domains forming a layered structure can be observed, exhibiting bi-directional orientation. This complex microdomain orientation can be explained by the balance of shear flow and extensional flow in different regions of the sample during the injection moulding process.

Such bi-directional microstructure more closely mimics the structure of a native heart leaflet and so is a desirable material for forming a prosthetic heart valve. Indeed, by linking the morphology to mechanical properties of the final solid material, a more refined approach to the fabrication of prosthetic heart valve leaflets, in particular, can be taken. Numerical modelling results has shown that even a small amount of orthotropy in the prosthetic material can significantly improve the mechanical behaviour of the valve, and that an appropriate orientation of the fibres can contribute to optimizing the stress distribution in the leaflets.

The present invention has identified that whilst valves produced by the single-shot moulding processing envisioned in WO 2015/128605 are easy to manufacture, a two-shot/over-moulding process provides unexpected key advantages.

Using two materials for the valve, one of the leaflets, one for the support structure or stent allows different parts to have different mechanical properties resembling more closely the native valve. This is advantageous because it allows the provision of different physical/dynamic properties to the different sections—for example, the stent can be made of a more rigid material than the leaflets, thereby allowing it to be on one end comparatively smaller and thinner compared to a case in which in the a heart valve is made entirely from the leaflet material, while on the other end remaining flexible enough to follow the dynamic performance of the native annulus after suturing during the cardiac systolic-diastolic cycle. However, there is a problem that using two different materials creates a possible point of weakness at the transition zone, which needs to be engineered accurately to prevent valve failure while enhancing its dynamic performance.

The inventors have surprisingly discovered that this problem can be addressed by using an over-moulding technique, using a different polymer for the leaflets, compared to the stent or supporting structure around the leaflets. Advantageously, this process also allows for valves to be produced in a broad range of sizes, by providing different sized moulds, whereas currently available valves are only available in a few sizes that may not be the best fit for a particular patient.

FIG. 1 shows the basic structure of a prosthetic heart valve 110. The valve 110 can be any type of prosthetic heart valve, e.g. for open heart surgical implant or a transcatheter heart valve, in any anatomic position (aortic, mitral, tricuspid, pulmonary).

The body of the valve 110 comprises a stent 111 comprising three posts 112 supported on a base or sewing ring 113. Three valve leaflets 114 each extend between and connect to two of the posts 112, with the base of each leaflet attached to the base 113 between the two posts to which it is connected. The leaflets 114 are for actuating the valve.

The leaflets 114 are shaped so that their tops meet in the middle of the valve 110. In use, blood flow from below (in the orientation of FIG. 1) the valve 110 will cause the leaflets to separate and allow the blood to pass through the valve 110, whereas any attempted flow in the other direction will force the leaflets 114 towards each other and thus close the valve 110.

Figure 9:
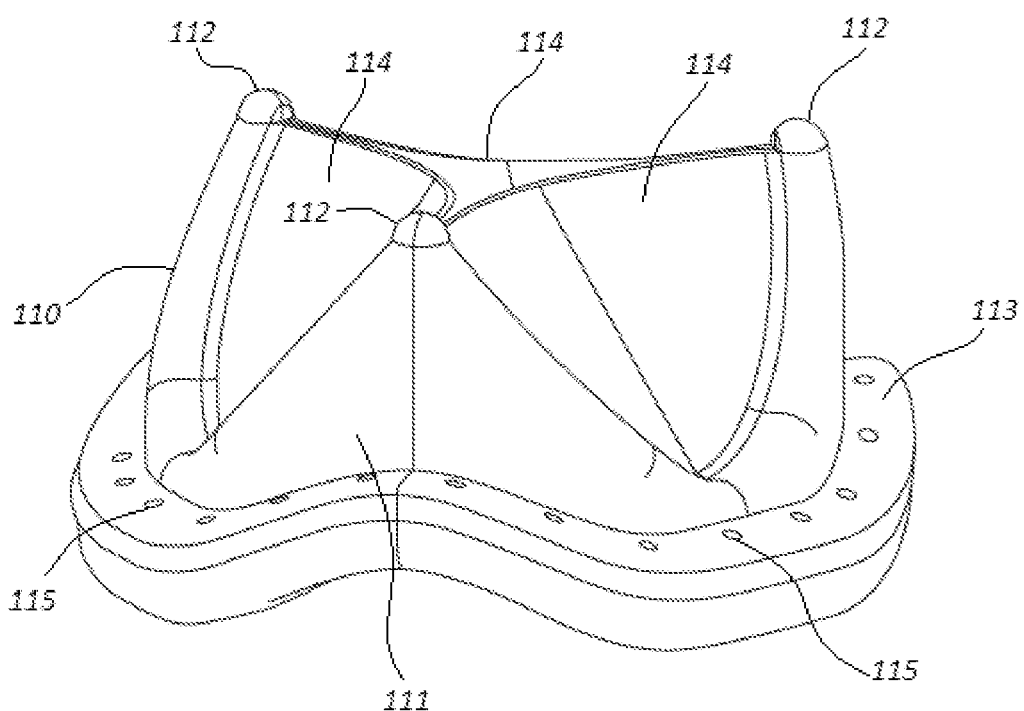
FIG. 9 is a schematic representation of another injection moulded heart valve according to an aspect of the present disclosure.

The shape of the leaflets 114 can be a cylindrical (FIG. 9) or spherical section, for example. The leaflets 114 may also be provided with thickened 'nodules' (not shown) at the centre of their free edge, to assist with sealing. The thickness of a leaflet 114 may vary across its surface from base to free margin. For example, a leaflet 114 may be thinner at its free edge, and thicker where it connects to the base 113, with a gradual change in thickness in between. The leaflets 114 may have a mean thickness in the range of 0.20 mm to 0.70 mm, optionally 0.3 mm to 0.50 mm, further optionally 0.37 mm to 0.42 mm.

Figure 2:
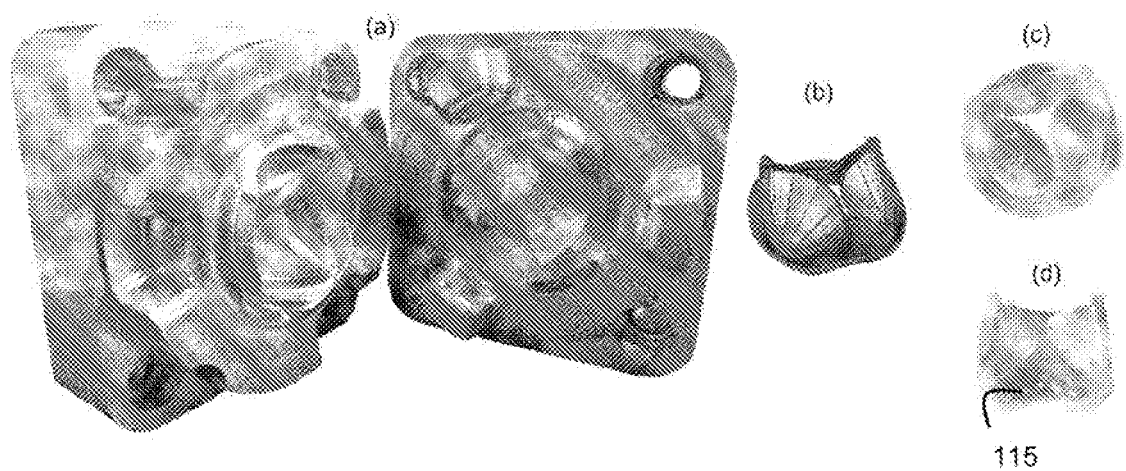
FIG. 2 shows (a) a picture of an aluminium mould insert for manufacturing a heart valve, (b) a CAD image of a valve produced by the mould (c) a photograph of a valve produced from the mould and (d) a photograph of the moulded valve with suture holes pre-formed into the sewing ring.

The base or sewing ring 113 is shown as a substantially circular in FIG. 1. However, it may have a more complicated shape, such a saddle-shape, to better fit the 3D contours of the valvular annulus and avoid its deformation after suturing. FIG. 2 illustrates a mould (FIG. 2(a)) and a valve (in CAD design in FIG. 2(b) and in photograph in FIGS. 2(c) and 2(d)) exhibiting such a saddle structure.

FIG. 2(d) also illustrates how suture holes 115 can be pre-formed into the sewing ring 113. These holes can assist a surgeon in more easily suturing the valve in place, while allowing the valve to not be fitted with a typical fabric sewing ring, thus avoiding a possible trigger of valve colonisation by bacteria. Such a sewing ring 113 is preferably semi-rigid/flexible so that after valve suturing the systolic-diastolic 3D motion of the valvular annulus is preserved. The particular location of the holes can be determined according to the particular patient (e.g. based on pre-surgical imaging) to provide them at appropriate points.

The entire valve shown in FIG. 1 can be manufactured by injection moulding. However, the heart valve may include non injection moulded elements (for example an underlying or supporting scaffold for the injection moulded element), which may be made of a different material to the injection moulded material. Preferably, the valve leaflets 114 are made by injection moulding BCP, although other methods may be used if they achieve the same result.

The valve 110, particularly the valve leaflets 114, has anisotropic physical properties on the macroscopic scale. This is because, as discussed above, the injection moulding process causes the BCP to aligned bidirectionally at the local level (or microscopic scale). The skilled reader will understand that the direction of the orientation in an absolute frame of reference will vary at different points on the leaflet due to the shape of the leaflet and the location of the injection moulding points in the mould (e.g. for the samples discussed above 'surface' orientation occurs radially, and so in different absolute directions at different points on the sample). Nonetheless, at the microscopic scale, the bidirectional orientation (in which the phase structure in the central layer is aligned substantially perpendicularly to the phase structure in the outer two layers) will be present, and at the macroscopic scale anisotropic properties are manifested (i.e. the variation in absolute alignment is not so varied as to be random—which would then result in isotropic properties). In particular, the Young's modulus is anisotropic.

Moreover, by using an over-moulding technique, the stent 111 can be made from a material different to that of the leaflets 114, allowing different bulk properties in the different parts.

The stent 111 can also be a block copolymer. Preferably, the BCP used in the stent 111 has the same constituent monomers, or blocks, as the BCP used in the leaflets. This unexpectedly promotes a good bond between the two parts in the over-moulding process. Without wishing to be bound by theory, it is thought that the phase structures of the two BCP materials (if they have the same constituent blocks) can merge at the interface between the two BCP materials, promoting the bonding. It is noted that the phase structure of the BCP materials need not be the same—for example the stent 111 could comprise (isotropic) spherical phase structures whilst the leaflets 114 could comprise (anisotropic) cylindrical phase structures.

In a further refinement, the sewing ring 113 can be made from a further different material to the stent and the leaflets, again to provide different bulk properties. That material can also be a BCP, allowing good bonding to the stent in an over-moulding step. As such, the sewing ring 113 can be more rigid than the stent 111, which in turn can be more rigid that the leaflets 114, without compromising the overall structural integrity.

In particular, styrenic BCPs are an advantageous class of BCPs to use for polymeric heart valves. Styrenic BCPS, including triblock copolymers, are synthetic thermoplastic elastomers amenable to high-throughput injection moulding, finding applications in many fields, including medical applications. They typically contain polystyrene "hard" domains in a continuous elastomeric phase (ethylene-butylene in SEBS—poly(styrene-block-ethylene/butylene-block-styrene); ethylene-propylene in SEPS—poly(styrene-block-ethylene/propylene-block-styrene)); with the hard domains forming physical cross-links and providing strength to the polymers, while the elastomeric phase gives flexibility and elasticity. Altering the relative fraction of hard and soft segments results in a wide range of morphologies at the nano-scale, driven by the immiscibility of the different blocks. Thus, by use of block-copolymers of various molecular weights and styrene fractions, a valve entirely polymeric, yet with a reinforced, semi-rigid/less flexible stent and more flexible leaflets can be made.

In particular, valves in which the stent is made of a semi-rigid/less flexible material than the leaflets can be produced. For example, a stent can be made from material with an (isotropic) Young's modulus that is at least 20 MPa more than the material of the leaflets, optionally at least 40 MPa more, still further optionally at least 50 MPa more.

Such polymeric valves can be been produced using plastic injection moulding techniques. Briefly, the overall process cycle comprises of following steps: melting of block copolymer granules, injection into the mould cavity in the form of a viscoelastic polymer flow, packing, cooling, and removing of the moulded part.

In an over-moulding process, in a two material valve (considered for ease of understanding, although the skilled person will understand that the process could be extended to a three material valve) the valve stent 111 can be manufactured first. This could occur in a separate mould to that used in the production of the overall valve 110, or could be done in the same mould, using different mould inserts.

The specific process conditions for manufacturing the stents 111 will vary for different materials. In general, when using a BCP material for the stent 111, the mould is heated to above the glass transition temperature but below the ODT. It will be understood, here and later in this document, that the 'glass transition' of interest is that of the more glassy BCP phase (in other words, the material with the higher glass transition temperature)—i.e. the PS phase in the example materials presented later in Table 1. The molten polymer can then be injection moulded, before the mould is cooled to below the glass transition temperature. As a result, the mould temperatures can typically be from 130° C. to 180° C., optionally from 145° C. to 160° C. The molten polymer may typically be at a temperature of 150° C. to 220° C., optionally from 165° C. to 200° C.

The step of injection moulding itself is preferably performed with a relatively slow injection rate. This helps preserve the phase separation in the BCP (which can be disrupted by high shear rates). For example, the injection moulding can occur at a volumetric flow rate of from 0.1 to 10 cm$^3$/s, optionally from 0.5 to 5 cm$^3$/s, further optionally from 1 to 3 cm$^3$/s.

By way of illustration, stents 111 made from Kraton® G1650 (SEBS29) (a cylinder-forming BCP, used in the examples discussed below) can be produced by heating a mould to around 155° C., and injecting the molten polymer at around 100 bar, at a melt temperature of around 195° C. An injection rate of around 1.27-2.54 cm$^3$/s can be used.

Alternatively, stents 111 made from Mediprene 520450 (a sphere-forming BCP from Hexpol AB) can be produced by heating the mould to around 148-150° C., and injecting the molten polymer at around 50 bar, a melt temperature of around 170° C. An injection rate of around 1.27-2.54 cm$^3$/s can be used.

The stent 111 can be injected, for example, via three symmetrically located injection channels. The injection points can be located on the posts 112, optionally at the top or bottom of the posts 112.

As a BCP is injected into the stent 111 below its ODT, a phase structure will be preserved. If the structure is anisotropic (e.g. cylinders) it will be aligned within the mould by the flow of the polymer, producing anisotropic physical properties in the stent 111 that mimic the structure of a natural heart valve. Alternatively, an isotropic (e.g. cylindrical nanophase) can be used, giving rise to more isotropic bulk properties that can be advantageous for the robustness of the valve.

If the stent 111 is produced in a separate mould to the overall valve 110, the stent 111 must be removed from its mould. As a result, the mould may be cooled to a temperature below the glass transition temperature of the polymer, to allow handling of the stent. Again, the particular temperature will depend on the particular polymer, but by way of example the mould may be cooled to at least 140° C., optionally 130° C. or 120° C. before the stent 111 is removed.

Subsequently, the leaflets 114 can be over-moulded on the stent 111. If the stent 111 has been produced in a different mould, the stent 111 is first positioned in the mould for the overall heart valve 110. Alternatively, if the same mould is being used, the mould is appropriately prepared (and e.g. any mould insert changed). Then the BCP material for the leaflets 114 can be injection moulded. Preferably a cylindrical nanophase is present in the leaflets 114, to produce the anisotropic structure and bulk properties that mimic a native heart. This means that the BCP typically has a minor volumetric phase fraction of around 0.1 to 0.3%, although this depends on the particular material.

Preferably, the BCP forming the stent 111 has a higher ODT than the BCP forming the leaflets, to avoid the phase structure in the stent 111 being lost when the over-moulding occurs.

In general, when using BCP materials, the mould is heated to above the glass transition temperature of the stent and leaflet materials but below the ODTs of both materials. Use of a suitably high mould temperature promotes bonding between the two moulded materials. For example, in the scenario of leaflet material G1642 (SEBS20) being moulded over a G1650 (SEBS29) stent (discussed below), a mould temperature of 150-155° C. was observed as resulting in valves more likely to fail at the junction between the leaflet and the stent, rather than within the material of the leaflet itself. Preferably, the minimum mould temperature is 40 to 60° C. higher than the melt temperature. Preferably the maximum mould temperature is 50 to 70° C. lower than the lowest ODT.

If starting with a separate stent 111 (i.e. as opposed to immediately over-moulding), the stent 111 can be heated in the mould to above the glass transition temperature of the stent BPC material, but below its ODT. This allows the phase structures of both materials to be preserved whilst also restoring some mobility to the stent material. When using BCP materials for the stent 111 and the leaflets 114 that are made of the same or similar constituent blocks, it is thought this mobility encourages mixing of the molecules from the two different BCP materials, in the phase structures at the interface between the two BCP materials, thus promoting a improved bond.

The second step of injection moulding is also preferably performed with a relatively slow injection rate. Not only does this help preserve the phase separation in the BCP (which can be disrupted by high shear rates), but it helps ensure the stent is not deformed by the injection of the leaflet material. The injection can be performed realised by three injection channels located symmetrically in the middle of each leaflet 114. That is, the injection points are located on the central axis of symmetry of each leaflet, halfway between the base and the free edge (the upper edge as shown in FIG. 1).

Preferably, the diameter of the injection channels should be smaller than the thickness of the leaflet. This ensures a secure detachment of the leaflet from the polymer remaining in the injection channel, when the valve is removed from the mould, without any damage to the leaflet.

By way of illustration, in the case of the materials used in the examples discussed below, a leaflet material G1642 (SEBS20) can be moulded over a G1650 (SEBS29) stent. After placing a separately formed stent in the mould, it can be heated for around 10 minutes in a mould at around 150-160° C. before injection of the leaflets.

In other cases, minimal stent pre-heating may be required. Returning to the Mediprene 520450 stent material mentioned above, that material exhibits a lower glass transition temperature, and so does not require any pre-heating: the stent can be placed in the mould right before injection of the leaflets (which will of course lead to the heating of the stent by the molten leaflet material).

In the example of using a leaflet material of G1642 (SEBS20), the leaflet material can be injected to the mould at a mould temperature of around 160° C., around 80 bar and a melt temperature of 190° C., and at an injection rate of around 1.27-2.54 cm$^3$/s.

After injection, there can be a period of annealing above the melt temperatures and below the ODTs of the stent and leaflet materials, to promote a good bond between the leaflets and the stents. The annealing period can be 1 minute or more, optionally 2 minutes or more, further optionally 4 minutes or more. The step of annealing can last for 10 minutes or less, optionally 8 minutes or less, further optionally 6 minutes or less.

The annealing period may also include some slow cooling. For example, a mould may cool from around 160° C. to 145° C. in air, in around 5 minutes.

After the annealing period, the mould may be actively cooled, e.g. via a water cooling system to set the valve. That is the valve is cooled below the glass transition temperature of the two constituent BCPs, allowing it's removal from the mould. Slow, passive cooling (in air cooling) has been found to leave undesirable cooling marks on the leaflets, as has low pressure injection of the leaflet material. Cooling marks are caused by shrinkage of the polymer during cooling. They are especially undesirable on a leaflet's surface, because they decrease the thickness of the leaflet compared to what is intended. Therefore, it is preferable to cool the valve by 20° C. or more at a rate of 10° C./min or more. In some cases, the cooling may involve cooling 50° C. or more at a rate of 10° C. or more. SEBS materials may be cooled, for example from around 160° C. to around 90° C. in around 5 minutes.

For a three component system, a more rigid SEPS (poly(styrene-block-ethylene/propylene-block-styrene)) material such as SEPS65 (e.g. Septon® 2104, from Kuraray Co., Ltd, Japan) can be used as the sewing ring, with SEBS29 as the stent material and SEBS20 as the leaflet material.

EXAMPLES

Materials

Commercial block copolymers SEPS (Kraton® G1730) and SEBS (Kraton® G1642, G1650) were used. Their basic molecular characterisation, evaluated by gel permeation chromatography (GPC), is presented in Table 1, along with information regarding the glass transition temperature of the poly(styrene) phase obtained by DMA analysis. Information regarding order-disorder temperatures is also presented, based on a value for SEPS22 taken from SB Chun et al., Macromolecules, 1999, 32 (12), pp 4030-4042 (1999) [doi: 10.1021/ma981665c) and with the other results obtained by temperature programmed rheometry.

TABLE 1

Molecular characterisation of materials.

| Material | Composition | Molecular weight (g/mol) | Styrene fraction (% wt) | PS Glass Transition Temperature (° C.) | ODT (° C.) |
|---|---|---|---|---|---|
| SEPS22 (Kraton ® G1730) | poly(styrene-block-ethylene/propylene-block-styrene) | 71697 | 19.2 | 100 | 230 |
| SEBS29 (Kraton ® G1650) | poly(styrene-block-ethylene/butylene-block-styrene) | 74837 | 28.4 | 120 | >310 |
| SEBS20 (Kraton ® G1642) | poly(styrene-block-ethylene/butylene-block-styrene) | 111327 | 19.6 | 112 | >310 |

Manufacturing

A summary of the geometrical and manufacturing features sampled is presented in Table 2, which presents the valves in their order of development, with the latest design being J6.

After using two commercial injection moulding tools manufacturers for prototypes F and B (see Table 2), aluminium mould inserts as shown in FIG. 2a, manufactured in the Whittle Lab (Aerospace Engineering) in Cambridge were used for further prototypes. This allowed for quick and low cost sampling of geometrical features at accuracy comparable, if not greater, to the professional tool making companies.

(contrast valves B, F, J1, J2, J3 with J4, J5), it is also dependent on valve design (e.g. contrast J1 and J2). Nonetheless, a significant enhancement has been achieved using a softer leaflet material in combination with a more rigid stent material—isotropic SEBS20 has a Young's modulus of around 4.5 MPa and isotropic SEBS29 has a Young's modulus of around 57 MPa. Having a semi-rigid/less flexible stent compared to the leaflets, but which can still move with the valvular annulus during the systolic-diastolic 3D motion is preferable compared to a much more rigid structure (such as existing totally rigid metallic valves).

Similarly, changing the injection point to the centre of the leaflet from previously utilised injection to the free edge

TABLE 2

Characteristics of tested heart valves.

| Valve | Single injection of SEPS22 | Overmoulding SEBS20 on SEBS29 stent | Injection to leaflets free edge | Injection to leaflets centre | Spherical leaflets | Cylindrical leaflets |
|---|---|---|---|---|---|---|
| B | X | | X | | X | |
| F | X | | X | | X | |
| J1 | X | | X | | X | |
| J2 | X | | X | | X | |
| J3 | X | | X | | X | |
| J4 | | X | | X | X | |
| J5 | | X | | X | | X |
| J6 | | X | | X | | X |

| Valve | Filet around leaflets | Concave leaflet free edge profile | Nodules in the middle of free edge | Heparin coating | Mean leaflets thickness, mm |
|---|---|---|---|---|---|
| B | | | | | 0.26 |
| F | X | | | | 0.37 |
| J1 | X | X | | | 0.36 |
| J2 | X | X | X | | 0.36 |
| J3 | X | X | | X | 0.36 |
| J4 | X | X | | | 0.35 |
| J5 | X | X | | | 0.22-0.48 |
| J6 | X | X | | | 0.40 |

As can be seen, several factors have been investigated, including the materials used, the position of injection moulding for the leaflets (the middle of the free edge of the leaflets vs the centre of the leaflet), the shape of leaflet (spherical section vs cylindrical section; presence of a thicker nodule in the middle of the free edge of the leaflets) and also the effect of coating the valve with heparin. The J6 valve represents an optimised leaflet thickness for the J5 design.

Durability

Durability of the valves was assessed in an accelerated fatigue tester (TA Electroforce) at 30 Hz with water as the working fluid at 37° C., under the test conditions by ISO 5840:2015, which require 100 mmHg pressure difference across the closed aortic valves for at least 5% of each cycle, and this should be maintained for more than 95% of all test cycles. Each valve was mounted in independently controlled testing chamber, where removal or adjustment of one sample did not affect other samples. Valve failure was identified by abnormal proximal and distal pressure traces and upon qualitative examination.

Figure 3:
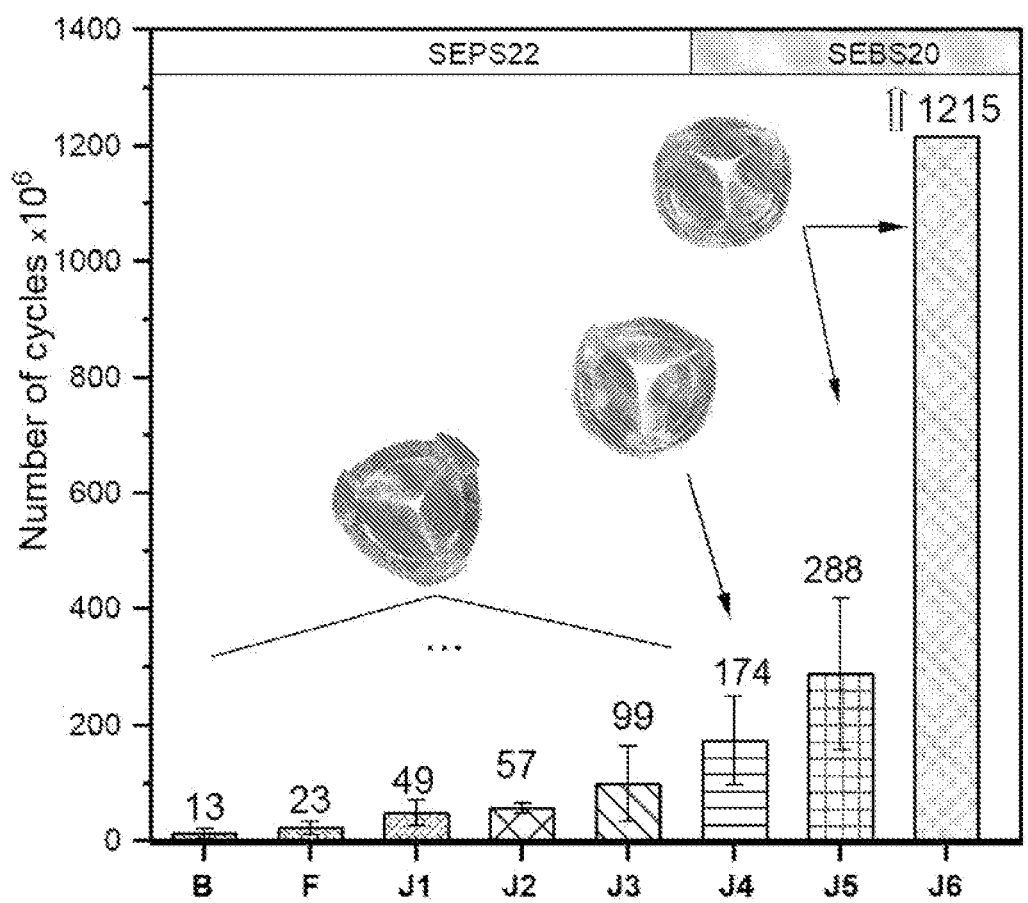
FIG. 3 is a graph illustrating the durability of different valve models.

FIG. 3 is a graph illustrating the durability of different valves characterised in Table 1.

Earlier valve models show insufficient valve durability with leaflet tears developing within a few tens of millions of cycles. As seen in FIG. 3, subsequent changes progressively improved their durability. Valve durability is not only a function of the polymer selected for leaflet construction (valves B-J3) is associated with an improved durability. It was observed that the failure mode of the valves changed, with the early valves often failing from the injection point on the free edge, whereas later valves injected at the leaflet centres were observed to have more varied failure points, indicative of a lack of a specific weak point.

Figure 4:
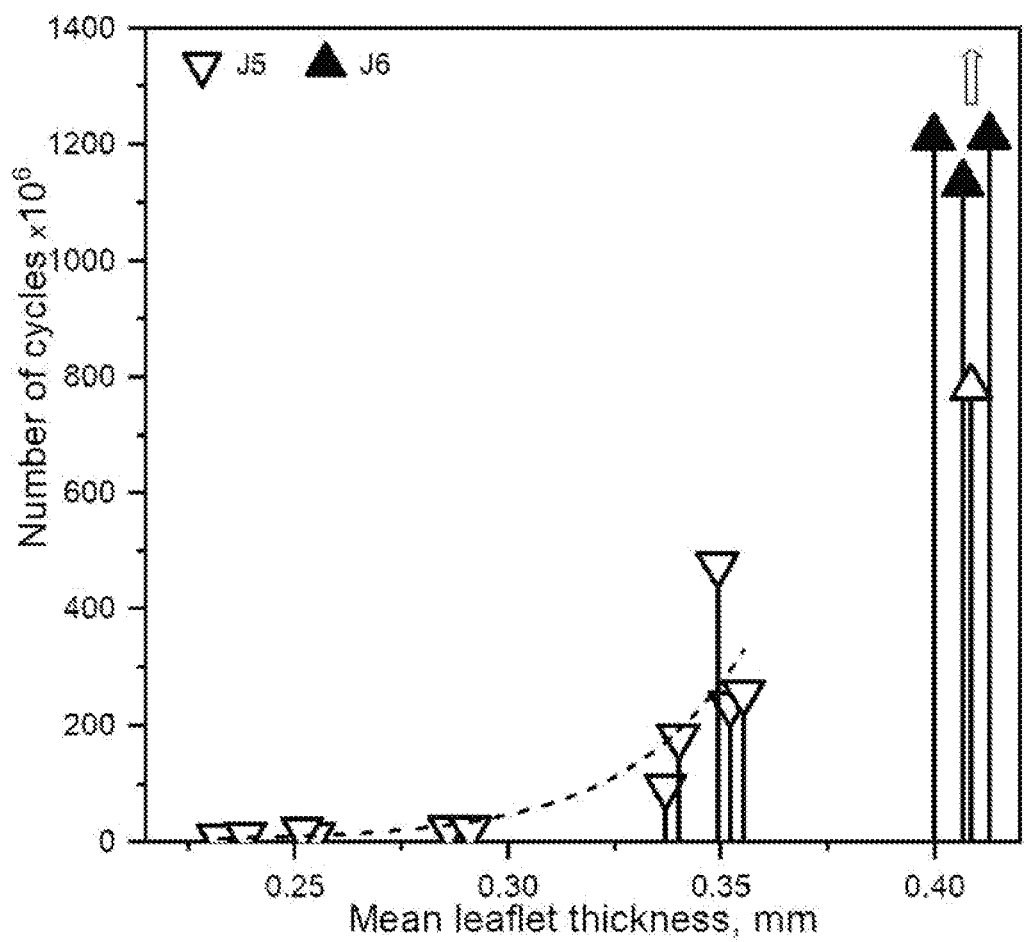
FIG. 4 is a graph illustrating the durability of a valve as a function of mean leaflet thickness.

Leaflet thickness is also relevant to the durability. FIG. 4 illustrates number of cycles an accelerated tester achieved for valves of the same design (J5) but with different leaflet thickness, along with the ongoing testing in the same tester for the J6 design. Shaded markers in FIG. 4 show ongoing testing while completed tests are represented by unfilled markers.

The thicker leaflets performed better in terms of durability but their opening area and transvalvular pressure gradient worsened as showed by hydrodynamic tests, discussed in the next section.

Four valves of the J6 design (two with 19 mm internal diameter and two with 21 mm internal diameter) were tested for durability. One of the J6 valves (v29) failed after 783 million cycles (the equivalent of over 20 years based on an assumption of 72 beats-per-minute). At the time of writing, the remaining three J6 valves are still being assessed in the heart valve durability tester; and have already comfortably passed minimum ISO requirements (200 million cycles), having exceeded 1 billion cycles (the equivalent of over 26 years).

Hydrodynamic Performance

Hydrodynamic performance of the polymeric valves was evaluated in a pulse duplicator system according to methodology described in De Gaetano et al. (Fluid Dynamic Performances of a New Polymeric Heart Valve Prototype (Poli-Valve) tested under Continuous and Pulsatile Flow Conditions, Int J Artif Organs 2015, 38(11), 600-606; DOI: 10.5301/ijao.5000452). Briefly, the pulse duplicator comprises of a volumetric pumping system, a ventricular chamber, an aortic valve housing, a systemic impedance simulator and a mitral valve housing. The pulse duplicator was able to reproduces the physiological stroke volume, pressure and flow waveforms.

Figure 5:
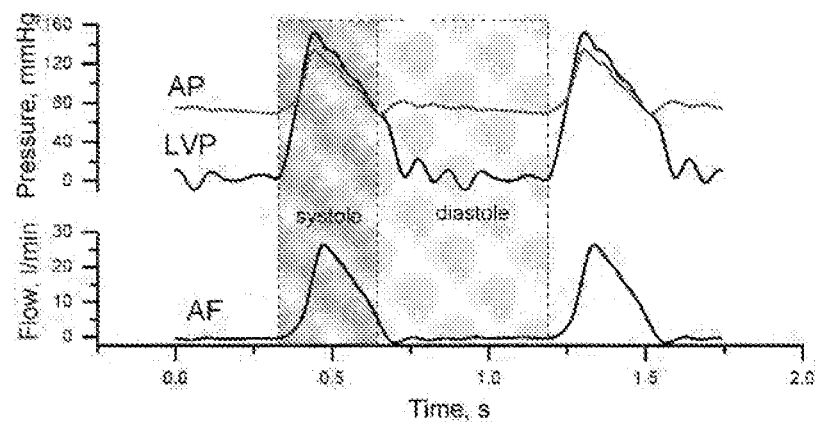
FIG. 5 is a graph illustrating pressure and flow tracings acquired during pulsatile tests of a J6 valve, where AP indicates aortic pressure, LVP indicates left ventricular pressure, and AF indicates aortic flow.

The polymeric valves were tested in aortic position with mechanical, tilting disc control valve mounted in the mitral position. The test conditions conformed to ISO 5840:2015 requirements i.e. frequency of 70 bpm, simulated cardiac output 5 l/min, systolic duration 35% at normotensive conditions. Simultaneous flow and pressure measurements upstream and downstream from the aortic valve were recorded by using Transonic ultrasound flowmeter and pressure transducers, respectively. An example of the pressure and flow tracings acquired during the pulsatile test of a J6 valve is presented in FIG. 5.

Hydrodynamic performance was evaluated by calculating the valves Effective Orifice Area (EOA) according to eq. (1) as per ISO 5840-2:2015, average systolic trans-valvular pressure drop (ΔP) and regurgitation fraction (REG).

$$EOA = \frac{Q_{RMS}}{51.6\sqrt{\frac{\Delta P}{\rho}}} \quad (1)$$

where the EOA is calculated in $cm^2$, $Q_{RMS}$ is the root mean square forward flow (ml/s) during the positive differential pressure period (ΔP>0), ΔP (mmHg) is the mean pressure difference (measured during the positive differential pressure period), and ρ (g/cm3) is the density of the test fluid.

The evaluated regurgitant fraction included closing volume, transvalvular leakage volume, and paravalvular leakage volume and was expressed as a percentage of the forward flow volume. The hydrodynamic testing was performed in comparison to a clinically-used Carpentier-Edwards Perimount Magna tissue valve of equivalent size (21 mm), which is commonly considered a gold standard reference valve.

Figure 6:
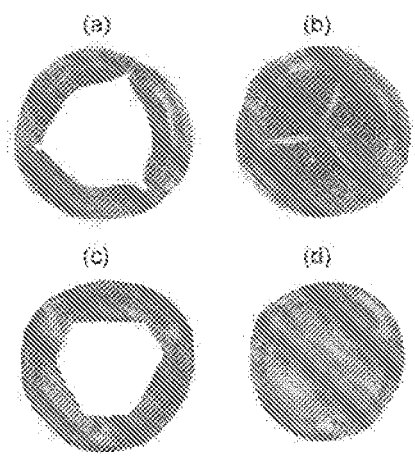
FIG. 6 shows pictures of a polymeric heart valve of type J6 at (a) systole and (b) diastole peak, and an equivalent size Perimount Magna valve at (c) systole and (d) diastole peak.

Photographs of the valves at peak diastole and systole are depicted in FIG. 6, allowing a qualitative comparison of the opening area at peak systole, as well as the shape of fully open orifice for both polymeric (J6) and reference valves.

The polymeric valve has a more circular opening and its geometrical opening area at the systole peak was about 15% larger than for the Perimount Magna valve. Nevertheless, the calculated mean values of EOA across six J6 polymeric valves was 1.77±0.005 $cm^2$, which was almost the same as for the mean EOA valve across two reference valves which was 1.76±0.13 $cm^2$. This indicates that the dynamic of opening for the two types of valves was different.

Figure 7:
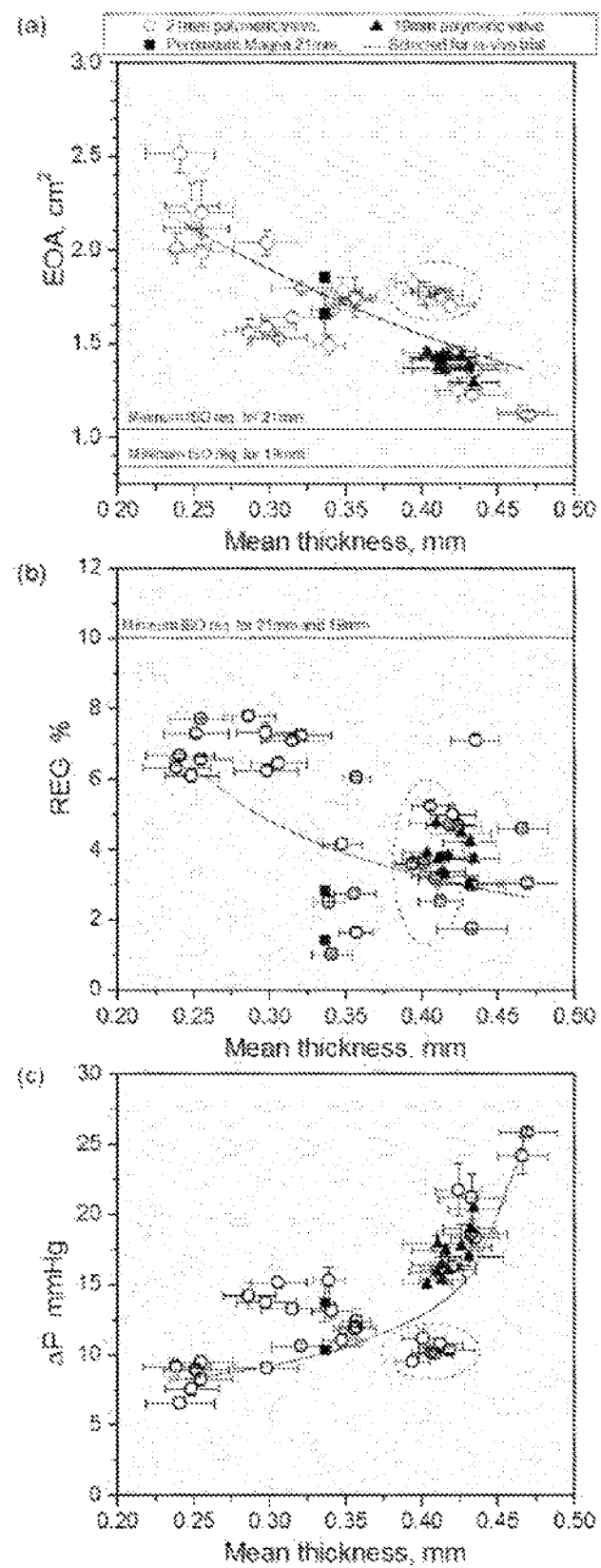
FIG. 7 shows how (a) EOA, (b), REG, (c) and mean systolic pressure gradient ΔP, vary for 21 mm polymeric valves of type J5 and J6 and an equivalent size reference Carpentier-Edwards Perimount Pericardial Bioprosthesis valve; a preferred J6 design selected for animal trial has been contoured by a dashes line, and an alternative size (19 mm) J6 valve is represented by triangular markers.

FIG. 7 presents the hydrodynamic performance of the J5 and J6, which incorporated the same geometrical features but various leaflet thicknesses. Five aluminium mould inserts were used to manufacture valves having average leaflets thickness of 0.24 mm, 0.30 mm, 0.35 mm, 0.40 mm and 0.46 mm respectively, so the effect of the thickness could be assessed. Six valves of each thickness were tested in the pulse duplicator system. All valves demonstrated satisfactory hydrodynamic performance, above minimum ISO standard requirements. Nevertheless the effect of thickness was substantial, especially for EOA, which reduced from 2.5 $cm^2$ to 1.1 $cm^2$ with increasing leaflet thickness from 0.24 mm to 0.46 mm (FIG. 7a).

Pressure gradient ΔP also considerably increased (from 8 to 25 mmHg) as the thickness increased from 0.24 mm to 0.46 mm (FIG. 7c). Test data for REG was more scattered, but the general trend showed a drop of regurgitation fraction with increasing thickness of the leaflets (FIG. 7b).

The Perimount Magna bioprosthetic valve's hydrodynamics, also shown in FIG. 7, approximately aligns with EOA and ΔP of polymeric valves of equivalent leaflet thickness. The bioprosthesis however showed slightly lower REG fraction (2.1±0.78%) than similar thickness polymeric valves (3.03±1.72%), which was still well below 10%—the ISO requirement for a 21 mm valve. Hence the leaflet thickness can optimised together with other geometrical features to reasonably balance durability and hydrodynamics of the valve. Based on the experimental test results, the J6 design with a leaflet thickness of 0.4 mm provides good durability with acceptable hydrodynamics (EOA=1.77±0.05 $cm^2$, REG=3.4±1.1% and ΔP=10±0.66 mmHg), comparable to biological valves currently used.

Figure 8:
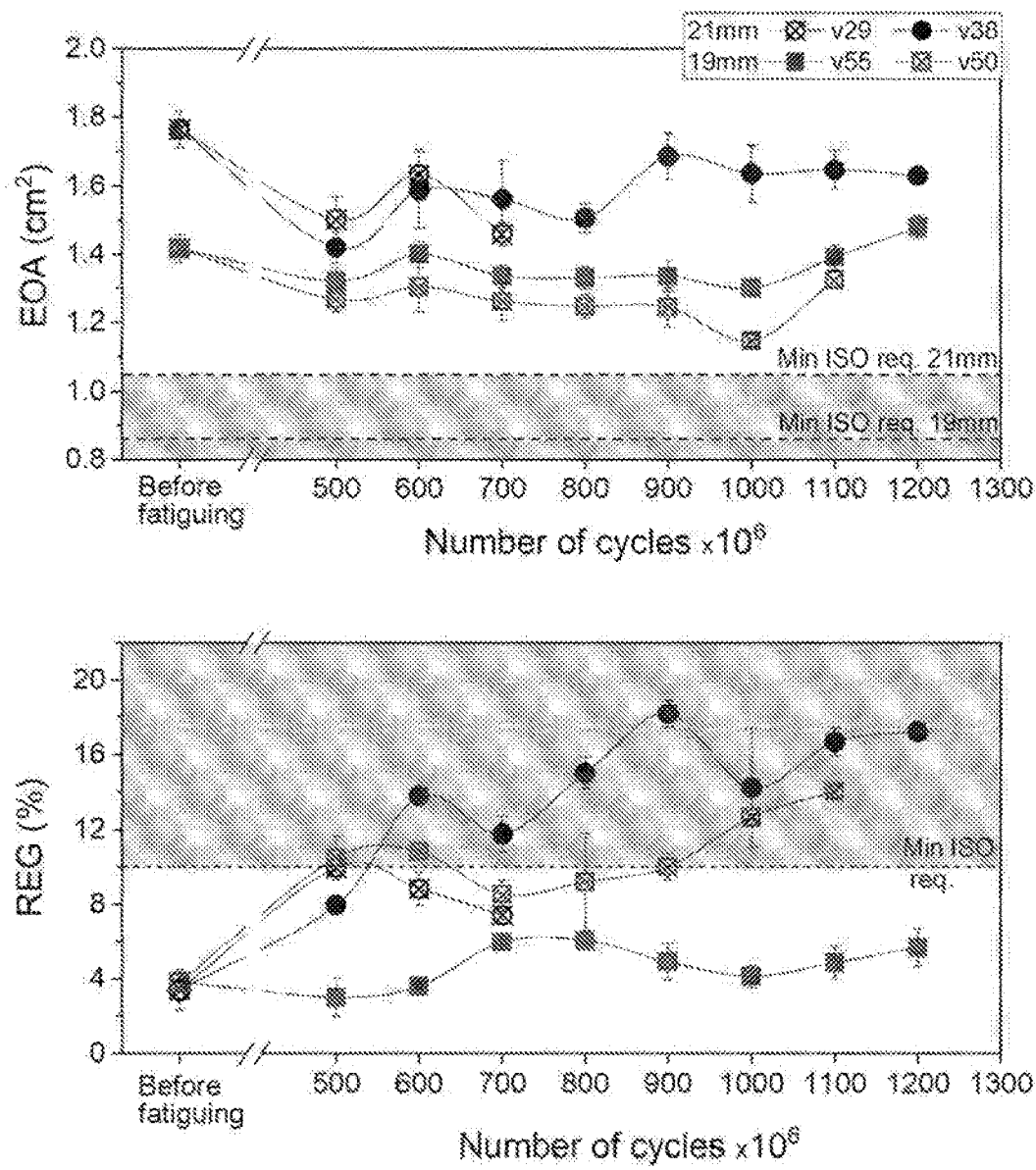
FIG. 8 shows how EOA and REG vary for polymeric heart valves of type J6 as the valves are fatigued during durability testing.

Hydrodynamic performance of each J6 valve was also measured before fatiguing and repeated after 500 million and then every 100 million cycles. The measurements of EOA and REG are presented in FIGS. 8A and B, respectively. Beyond 500 million cycles the opening area decreased by 10-15% compared to before fatiguing; the EOA of the valves remained well above the minimum required by ISO standards (0.85 cm2 for 19 mm and 1.05 cm2 for 21 mm). The free edge of three of the valves (v29, v38 and v50) started to show some damage beyond 500 million cycles, resulting in a somewhat increased regurgitation fraction. One of the 21 mm valves (v38) started to regurgitate >10% at 600 million cycles and gradually worsened to 1.2 billion cycles. At 1 billion cycles one of the 19 mm valves (v50) also exceeded the 10% regurgitation limit specified by ISO standards for surgical valves and this continued at 1.1 billion cycles. Nevertheless after 1.1 billion (v50) and 1.2 billion cycles (v38) the regurgitation fraction was still smaller than 20%, which is the maximum allowed by ISO for transcatheter valves. It is thus anticipated that valves performing in this way would not significantly compromise the health of a patient, while having high potential to improve it. One of the 19 mm valves (v55) remained fully functional as required by ISO at 1.2 billion cycles (EOA=1.48 cm2, REG=5.66%). Fatigue data for this test was collected for over 17 months at 30 Hz; 1.2 billion cycles are equivalent to over 30 years of operation at 72 bpm.

Preliminary Clinical Feasibility Evaluations

Extra-vivo refinement of the polymeric valves was carried out to determine optimal characteristics of 3D shape, low profile, external diameter, flexibility/elasticity and suturability.

A series of surgical implantations and size-matching procedures were performed on pre-sized aortic annulus in porcine hearts/cadavers, informing the changes implemented from prototype B through J4 to prototype J6. The external diameter of a typical polymeric valve with an internal diameter of 21 mm was reduced from 32 mm to 25 mm. The base shape changed from 2D flat to 3D saddle-shape to reflect the 3D lining of the porcine/human aortic valve annulus, while the height/profile was reduced to 13 mm. The consistency of the polymeric valves changed from rigid/semi-rigid to flexible/elastic to aid in preserving the physiologic dynamics of the native valvular annulus after implant. A fabric-free valve suturing system was achieved, based on 12-14 pairs of holes (0.5 mm diameter) as shown in FIG. 2b)-d), which allowed excellent extra-vivo implantation of J6 without deformation.

Extra-vivo compatibility to magnetic resonance imaging (MRI) was assessed by suturing two polymeric valves in two porcine hearts in aortic and mitral positions. The polymeric valve inserted in the mitral position was intentionally sutured over the native mitral valve to allow direct comparative imaging evaluations with the native leaflets. This experiment showed excellent MRI compatibility of the polymeric valve, and allowed a detailed morphological assessment of the polymeric valve with no artefacts. Finally, the compatibility of the polymeric valve with clinical sterilisation techniques was assessed by bench based evaluation with and without sterilisation, and the durability and hydrodynamic performance of the sterilised PHV was not adversely affected.

An in-vivo short-term feasibility study was carried out in 75-80 kg sheep in a model of cardiac surgery with CPB and CA through left thoracotomy with a recovery time ranging from 1 to 24 hours. In all cases a 19 mm J6 polymeric valve was inserted in supra-annular fashion using 4-0 prolene sutures. In-vivo echocardiographic evaluations were recorded at 1 hour post-surgery, with an ongoing average systolic blood pressure of 96±8 mmHg. There was no evidence of any peri-valvular or trans-valvular regurgitation. Measurements of the average trans-valvular peak gradient indicated 23±3 mmHg, in keeping with the bench-based hydrodynamic performance of the 19 mm J6 valve.

One of these 3 animals was kept for 24 hours after completion of surgery and extubated successfully for post-extubation safety assessment of short-term valvular integrity and biocompatibility. This animal was not anticoagulated and received only Aspirin 300 mg/day. Post-mortem confirmed intact structure of the polymeric valve with no evidence of any acute valvular clot/thrombus.

The skilled person will understand that the foregoing description has focussed on particular examples of the invention, and that invention is not limited to those examples. The invention is defined in the claims.

What is claimed is:

1. A method of manufacturing a heart valve, the method comprising:
    a step of injection moulding a first part of the heart valve from a material comprising a first block-copolymer, wherein the injection moulding is performed at a temperature below an order-disorder transition temperature of the first block copolymer, such that a phase structure is present in the molten block-copolymer;
    a step of injection moulding a second part of the heart valve from a material comprising a second block-copolymer that is different to the first block-copolymer, by over-moulding over the first part to form an over-moulded structure, wherein the injection moulding is performed at a temperature below order-disorder transition temperatures for the first and second block copolymers, such that a phase structure is present in the molten second block-copolymer and remains present in the first block-copolymer; and
    a step of cooling the over-moulded structure, without heating it above the order-disorder transition temperatures between the step of injection moulding the second part and the step of cooling, so as to preserve an arrangement of the phase structures created during the steps of injection moulding and produce anisotropic physical properties in the second part.

2. A method according to claim 1, wherein the first block copolymer has a higher order-disorder temperature than the second block-copolymer.

3. A method according to claim 1, wherein the first and second block-copolymers are composed of the same constituent monomers.

4. A method according to claim 1, wherein the first and second block-copolymers are both sytrenic block-copolymers.

5. A method according to claim 1, further comprising a step of annealing the over-moulded structure after the step of injection moulding the second part.

6. A method according to claim 5, wherein the step of annealing comprises maintaining the over-moulded structure at a temperature below the order-disorder temperatures of the first and second copolymers and above glass transition temperatures of the first and second copolymers.

7. A method according to claim 5, wherein the step of annealing lasts for 1 minute or more.

8. A method according to claim 5, wherein the step of annealing lasts for 10 minutes or less.

9. A method according to claim 1, wherein the step of cooling comprises lowering the temperature of the over-moulded structure below glass transition temperatures of the first and second block-copolymers.

10. A method according to claim 1, wherein the step of cooling comprises lowering the temperature of the over-moulded structure by 20° C. or more at a rate of 10° C./min or more.

11. A method according to claim 1, wherein the step of cooling occurs before the over-moulded structure is removed from the mould.

12. A method according to claim 1, wherein the first and/or second step of injection moulding occurs at a volumetric flow rate of from 0.1 to 10 cm³/s.

13. A method according to claim 1, wherein the second part comprises heart valve leaflets.

14. A method according to claim 13, wherein an injection point for the step of injection moulding the second part is at a centre point of the leaflet.

15. A method according to claim 13, wherein each of the leaflet define a portion of a cylinder.

16. A method according to claim 13, wherein the leaflet has a mean thickness in the range of 0.20 mm to 0.70 mm.

17. A method according to claim 1 wherein the second block-copolymer has a lower Young's modulus than the first block-copolymer.

18. A method according to claim 1, wherein the first part comprises a stent.

19. A heart valve comprising:
    a first part formed from a material comprising a first block-copolymer exhibiting a phase structure formed by its constituent blocks; and
    a second part formed from a material consisting essentially of a second block-copolymer that is different to the first block-copolymer, the second block copolymer exhibiting a phase structure formed by its constituent blocks,
    wherein the phase structure of the second block-copolymer is arranged so as to produce anisotropic physical properties in the second part.

20. A heart valve according to claim 19, wherein the second part comprises a heart valve leaflet.

21. A heart valve according to claim 20, wherein the valve leaflet has a variable thickness across its surface.

22. A heart valve according to claim 19, wherein the first part comprises a stent.

23. A heart valve according to claim 22, wherein the stent comprises a sewing ring.

24. A heart valve according to claim 23, wherein the sewing ring comprises holes for passing a sewing needle through.

\* \* \* \* \*